United States Patent [19]
Schirch

[11] Patent Number: 6,046,017
[45] Date of Patent: Apr. 4, 2000

[54] RAPID AND SENSITIVE ASSAY FOR HOMOCYSTEINE

[75] Inventor: LaVerne Schirch, Mechanicsville, Va.

[73] Assignee: Virginia Commonwealth University, Richmond, Va.

[21] Appl. No.: 09/332,510

[22] Filed: Jun. 14, 1999

[51] Int. Cl.[7] .............. C12Q 1/26; C12Q 1/32; C12Q 1/48; C12Q 1/00
[52] U.S. Cl. .............. 435/25; 435/26; 435/15; 435/975; 435/4
[58] Field of Search .............. 435/25, 26, 15, 435/975, 4

[56] References Cited

PUBLICATIONS

Steen et al, "Prenatal Diagnosis", vol. 18 (6), p545 (Abstract), Jun. 1998.

Sturman et al; J. Neurochem., vol. 27 (2), p425 (Abstract), 1976.

*Primary Examiner*—Louise N. Leary
*Attorney, Agent, or Firm*—Whitham, Curtis & Whitham

[57] ABSTRACT

Methods and kits for assaying homocysteine in biological samples utilizing enzymatic reactions are provided. One method utilizes the enzymes methionine synthase and serine hydroxymethyltransferase sequentially to produce $^3H_2O$ in proportion to the amount of hCys in the original sample. Another method utilizes the enzyme methionine synthase and then the enzymes serine hydroxymethyltransferase, methylene tetrahydrofolate dehydrogenase and formyl tetrahydrofolate dehydrogenase, to produce NADPH in proportion to the amount of hCys in the original sample.

17 Claims, 7 Drawing Sheets

RAPID AND SENSITIVE ASSAY FOR HOMOCYSTEINE

This invention was made using funds from grants from the National Institutes of Health having grant number GM28143. The government may have certain rights in this invention.

BACKGROUND OF THE INVENTION

1. Field of the Invention

The invention generally relates to the detection of homocysteine. In particular, the present invention provides rapid and sensitive methods for the detection and quantification of homocysteine in plasma and tissue.

2. Background of the Invention

Abnormally elevated levels of the amino acid homocysteine (hCys) in plasma and tissue extracts are related to many serious pathological conditions. For example, recent observations have demonstrated a relationship between hyperhomocysteinemia and coronary heart disease (1–3) and neural tube defects (4,5). Elevated levels of hCys are even more pronounced with other compromised organ or medical conditions, for example, heart transplants (6), end-stage renal disease (7), Parkinson's disease (8), diabetes (9), and preclampsia and fetal growth restriction (10). The exact relationship of elevated plasma hCys levels to these diseases is unknown and is the subject of intense investigation. The relationships are likely to be complex, as indicated by recent studies showing that hCys effects such diverse biological processes as mitochondrial gene expression (11), the secretion of cholesterol in hepatic cells (12), and leucovorin and 5-fluorouracil therapy in cancer patients (13).

Figure 1:
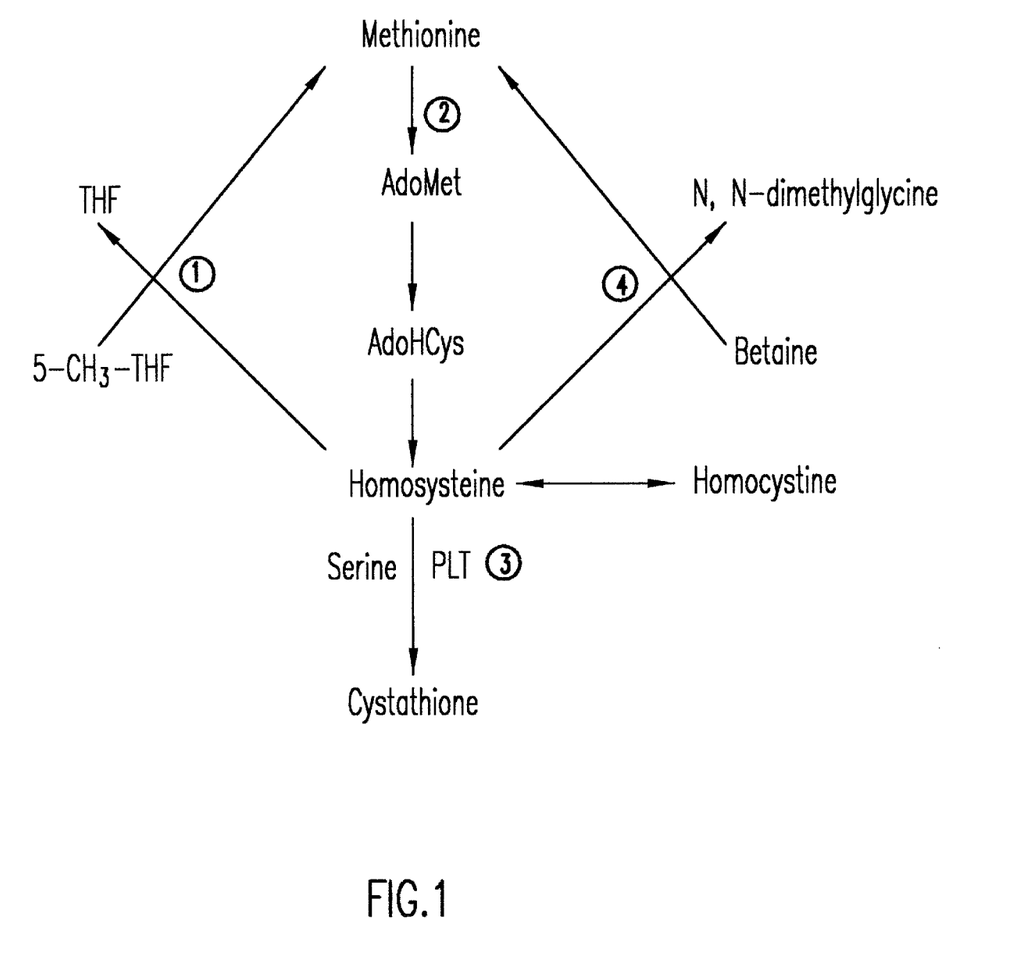
FIG. 1. Metabolic pathways for the formation and breakdown of hCys.

Homocysteine is the precursor of the amino acid methionine and the metabolic pathways for the formation and breakdown of hCys are illustrated in FIG. 1. High levels of hCys can be caused by an impairment in any one of several enzymes involved in the metabolism of this amino acid. For example, a defect in the enzyme methionine synthase, which catalyzes Reaction 1 in FIG. 1, results in a buildup of hCys and inadequate supplies of methionine and adenosyl methionine (AdoMet). The inability to convert hCys to methionine can also be caused by an inadequate supply of either the substrate 5-methyltetrahydrofolate (5-CH$_3$-THF) or low vitamin B$_{12}$, caused either by low folate nutrition or a defect in the enzyme methylenetetrahydrofolate reductase. Recent studies have demonstrated that low folate intake by pregnant women results in a several-fold increase in births of children with neural tube defects (4,5). The addition of folate to the diet frequently results in a lowering of the plasma hCys level. In some cases, both vitamin B$_{12}$ and B$_6$ can lower hCys levels. The effect of B$_6$ is usually ascribed to the enzyme β-cystathionase, an enzyme in the degradation pathway of hCys (Reaction 3 of FIG. 1).

As mentioned above, hyperhomocysteinemia is usually associated with low AdoMet levels. Low AdoMet levels can have devastating physiological consequences because AdoMet is the only methyl donor in the cell capable of methylating DNA, RNA, proteins, and numerous small molecules, many of which are precursors to neurotransmitters. (Although betaine can serve as a methyl donor in liver and kidney, this appears to be a minor pathway.) Thus, an individual with low AdoMet is at risk for a number of health problems.

Given the widespread health problems associated with elevated levels of hCys, it would be advantageous to have a rapid, inexpensive assay for detecting and quantifying hCys to be used in both clinical and research settings. The two major methods currently used do not fulfill these criteria in that they are both time-consuming and expensive.

Figure 2:
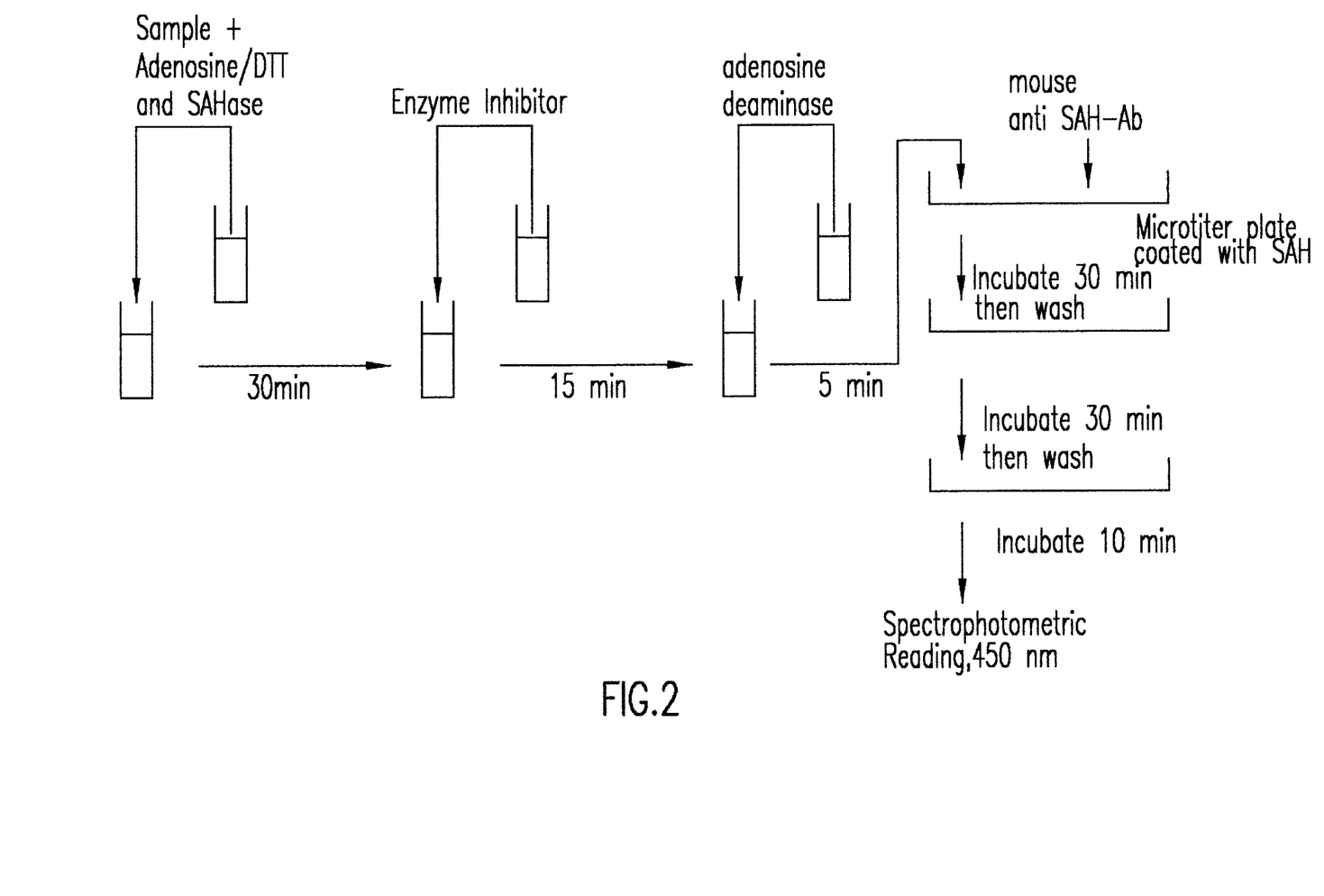
FIG. 2. Schematic of currently used automated assay for hCys.

Most of the hCys in plasma is protein-bound as disulfide and thus must be released by reduction prior to analysis. The most common currently-used method of detection reduces the hCys disulfide with dithiothreitol, enzymatically converts the hCys to S-adenosyl homocysteine, and detects the S-adenosyl homocysteine using monoclonal antibodies in an enzyme-immunosorbent assay (EIA)(14). The level of sensitivity of this assay is about 0.2 nmoles. The entire automated procedure, which has a 2.5 hour assay time, is presented in FIG. 2.

This method is available as a kit from Abbott Labs; the cost of each assay is about $10.00, not including the labor charge of the clinical lab making the measurement.

The second common procedure treats the reduced plasma with a derivatizing agent such as 4-aminosulfonyl-7-fluoro-2,1,3-benzoxydiazole, which forms a fluorescent adduct with the sulfhydryl group of hCys. (Note that dithiothreitol cannot be used in this assay because it interferes with subsequent HPLC analysis.) The fluorescent adduct of hCys is then separated by high performance liquid chromatography (HPLC) and the area under the peak corresponding to the hCys adduct is used to calculate the amount of hCys in the original plasma (15). This method requires 14 minutes to reduce the disulfide, 5 minutes for centrifugation, and up to 30 minutes for HPLC. Thus, nearly one hour is required to make a single determination. The level of sensitivity of this method is about 1 nmole. This procedure is available as a kit from BioRad at a cost of $7.00 to $7.50 per assay. For many labs doing research in this area, it is not uncommon to do 1000 hCys assays to obtain the data for a single publication. The cost would be at least $7000 using this method and require about 1000 hours of analysis time, since the procedure is not readily automated to accommodate large numbers of samples. Yet this is by far the method most often used in research laboratories.

The demand for assays of hCys is increasing. For example, the number of research publications about hCys has increased every year since 1990, from about 100 in 1990 to nearly 600 in 1998. During January and February of 1999 alone, over 100 hCys papers were published. This is clear evidence of a trend toward increased interest in hCys and the need for improved methods of assaying for hCys increases concomitantly. Likewise, hospital clinical labs such as that at the Medical College of Virginia anticipate that the demand for the analysis of hCys may approach that of cholesterol in the near future (private communication).

It would be a distinct advantage to have available rapid, sensitive and economically feasible methods for quantifying the level of hCys in biological samples. Such methods would be useful to both researchers in the scientific community and to clinical diagnosticians.

SUMMARY OF THE INVENTION

The object of this invention is to provide rapid, sensitive and economically feasible methods for quantifying hCys in samples. In one method (Method 1), hCys in a sample solution is measured by the steps of combining the sample solution with 5-CH$_3$-THF in the presence of the enzyme methionine synthase, forming the reaction product THF, reacting the reaction product THF with tritiated glycine in the presence of water using the enzyme serine hydroxymethyltransferase to form tritiated water and non-tritiated glycine, and quantifying the amount of tritiated water which is formed. The tritiated water is separated from the unreacted tritiated glycine by exposing the reaction mix to a solid support such as Dowex-50 resin. The 5-CH$_3$-THF of the reaction is present in molar excess.

In another method (Method 2), hCys in a sample solution is measured by the steps of combining the sample solution with 5-CH$_3$-THF in the presence of the enzyme methionine synthase, forming the reaction product THF, reacting the reaction product THF with serine and NADP$^+$ in the presence of the enzymes serine hydroxymethyltransferase, methylene tetrahydrofolate dehydrogenase and formyl tetrahydrofolate dehydrogenase, and measuring the NADPH produced.

For both Methods 1 and 2, endogenous folates may be removed prior to the reactions, and the sample may be reduced prior to carrying out the reactions. In both methods, the reactions may be carried out sequentially or simultaneously.

ABBREVIATIONS hCys, homocysteine; AdoHCys, adenosyl homocysteine; DTT, dithiothreitol; SAHase, S-adenosyl homocysteinase; SAM, S-adenosyl methionine; AdoMet, adenosyl methionine; THF, tetrahydrofolate (5,6,7,8-tetrahydropteroyl-L-glutamic acid); 5-CH$_3$-THF, 5-methyl tetrahydrofolate; PLP, pyridoxal phosphate; EIA, enzyme-immunosorbent assay; SHMT, serine hydroxymethyltransferase; ELISA, enzyme-linked immunosorbent assay; Met, methionine; Ser, serine; Gly, glycine; 10-CHO-THF, 10-formyl-tetrahydrofolate; CH$_2$-THF, methylene tetrahydrofolate; TCA, trichloroacetic acid; [2-$^3$H]glycine, tritiated glycine; NADPH, nicotinamide adenine dinucleotide phosphate (reduced); NADP$^+$, nicotinamide adenine dinucleotide phosphate (oxidized).

DETAILED DESCRIPTION OF THE PREFERRED EMBODIMENTS OF THE INVENTION

The present invention provides two methods for quantifying hCys by utilizing a series of enzymatic reactions.

METHOD ONE

Figure 3:
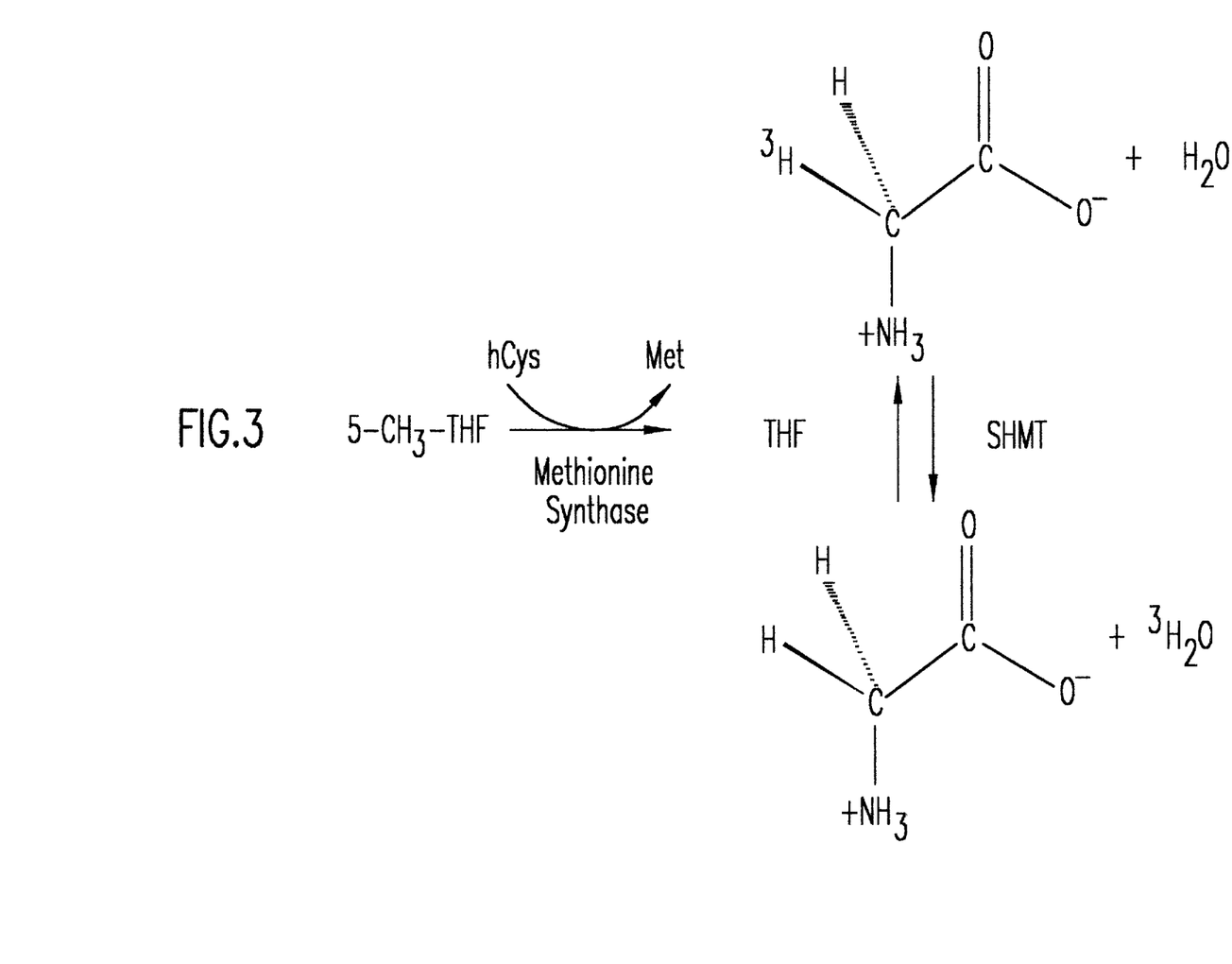
FIG. 3. Schematic of the reactions used for measuring one-carbon derivatives of folates in tissue extracts.

Method 1 employs two sequential enzymatic reactions to quantify hCys. The first enzyme is methionine synthase, which catalyzes the reaction shown in Equation 1 (Reaction 1 of FIG. 3).

Equation 1

When methionine synthase and 5-CH$_3$-THF are present in excess in a reaction mixture, all hCys in the mixture is quantitatively converted to methionine, with the concomitant generation of an equimolar amount of THF. Thus, the amount of THF which is formed is directly proportional to the amount of hCys present in the original reaction. The first enzymatic step of Method 1 is the conversion of hCys in, for example, tissue extracts or plasma, to THF.

The second enzymatic step in Method 1 utilizes the enzyme serine hydroxymethyltransferase (SHMT). SHMT catalyzes the reaction shown in Equation 2.

Equation 2

SHMT also forms an abortive complex with the product glycine and the substrate THF. In so doing, SHMT catalyzes the slow solvent exchange of the α-proton of glycine (Reaction 2 of FIG. 3), so that, when the position of the α-proton of glycine is occupied by tritium, the tritium is removed from glycine and "exchanged" with a proton from solvent H$_2$O, producing $^3$H$_2$O and non-tritiated glycine. The rate of exchange is increased by more than three orders of magnitude in the presence of THF (16). Thus, in the presence of excess SHMT and [2-$^3$H]glycine, the extent of exchange is directly proportional to the amount of available THF. It is possible to monitor the extent of $^3$H exchange (and thus the amount of THF) in a reaction by quantifying the amount of $^3$H$_2$O produced in the reaction. From equations 1 and 2, it should be apparent that when used in conjunction with methionine synthase, SHMT can be used to determine the concentration of hCys in biological samples.

Method 1 of the present invention uses the enzymes methionine synthase and SHMT to detect and quantify hCys in biological samples. Briefly, an excess of methionine synthase and of 5-CH$_3$-THF is added to a reaction mixture. Because the enzyme and 5-CH$_3$-THF are in excess, all of any substrate hCys present in the mixture will be quantitatively converted to methionine and an equimolar amount of THF will be generated (Reaction 1 of FIG. 3). The amount of THF generated by the first reaction is then quantified using the enzyme SHMT. An excess of SHMT and [2-$^3$H] glycine are added to the reaction and $^3$H$_2$O is produced in proportion to the amount of available THF (Reaction 2 of FIG. 3). Under the conditions of Method 1, the final amount of $^3$H$_2$O is thus directly proportional to the amount of hCys in the original sample.

Figure 4:
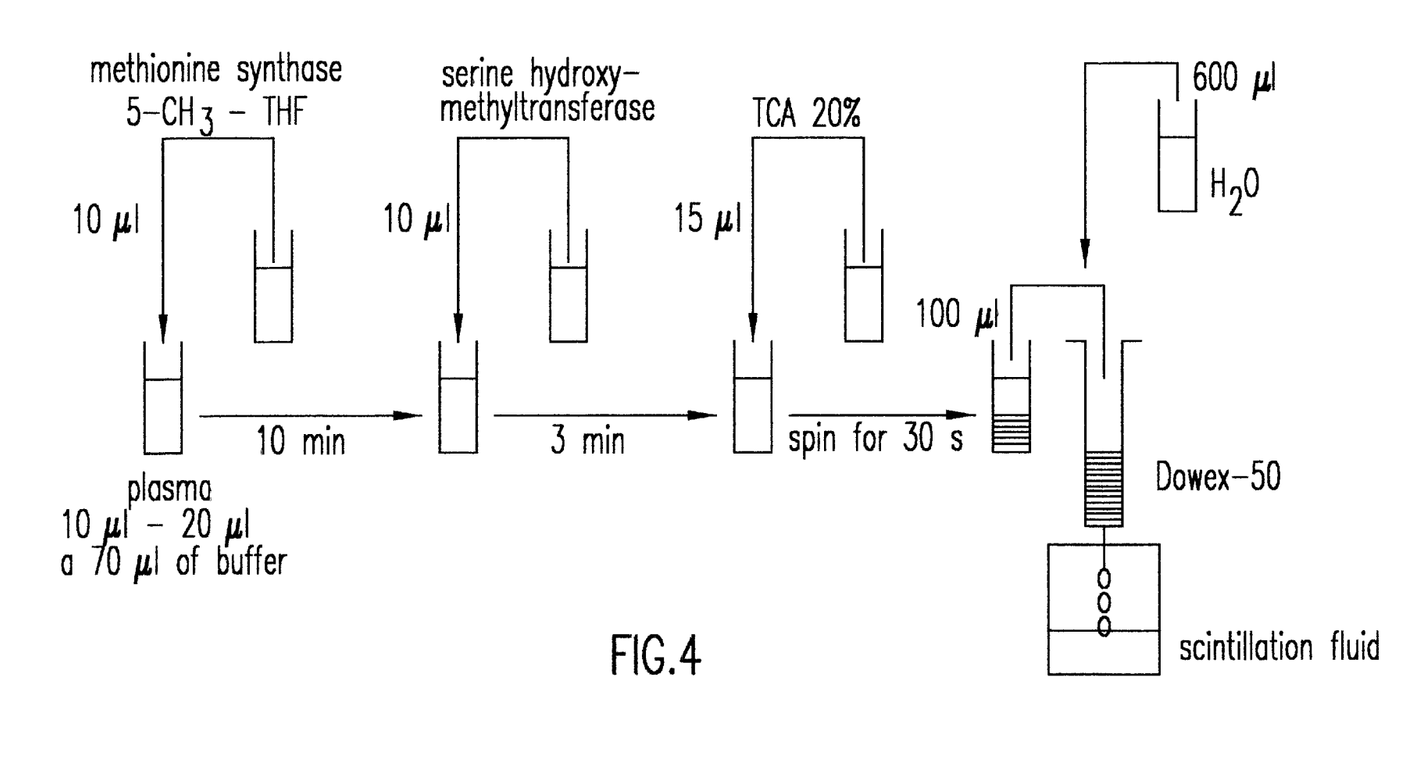
FIG. 4. Schematic for the procedure for determining hCys concentrations using the [$^3$H] glycine exchange assay (Method 1).

In a preferred embodiment, Method 1 can be practiced as follows: First, if the biological sample of interest is tissue, it is extracted with dilute acetic acid, which destroys all of the endogenous folates, and then the extract is neutralized. This step is performed in two minutes. For samples of serum or plasma this extraction step is not required since the levels of hCys greatly exceed the levels of endogenous folates. Dithiothreitol (DTT, 5 mM) is added to the sample to reduce all disulfides of hCys. A small aliquot (usually 10–20 μl) is removed and added to a vial containing methionine synthase (about 20 μg) and 5-CH$_3$-H$_4$THF (about 10 nmoles) in about 70 μl of buffer, and incubated for 10 minutes at 30° C. During this preincubation, the hCys and 5-CH$_3$-H$_4$THF are converted to methionine and THF. SHMT (200 μg) and [2-$^3$H] glycine (about 1×10$^6$ cpm) are then added to this solution and the solution is incubated another 3 min at 30° C. During this incubation, the α-proton of [2-$^3$H] glycine is exchanged with solvent H$_2$O to form $^3$H$_2$O, in proportion to the amount of THF that is present. The reaction is stopped by the addition of 10 μl of 10% TCA and the tube is centrifuged in a microfuge for 30 sec. The supernant is transferred to a small (5 mm high in a 1 ml syringe) Dowex-50 column equilibrated in 0.1 M HCl. The column is washed with 500 μl of H$_2$O and the effluent is collected in a scintillation vial and counted in a scintillation counter. FIG. 4 shows a schematic of this procedure. This sequential enzyme Method 1 requires no separation steps and does not require the derivatization of hCys. The total assay time is approximately 30 minutes or less (we currently assay 6 samples in about 20 minutes) and the assay is sensitive in the 0.1 to 2 pmole range. Because Method 1 utilizes radioactive isotopes, it is likely to be best suited for use in a research setting.

METHOD TWO

Figure 5:
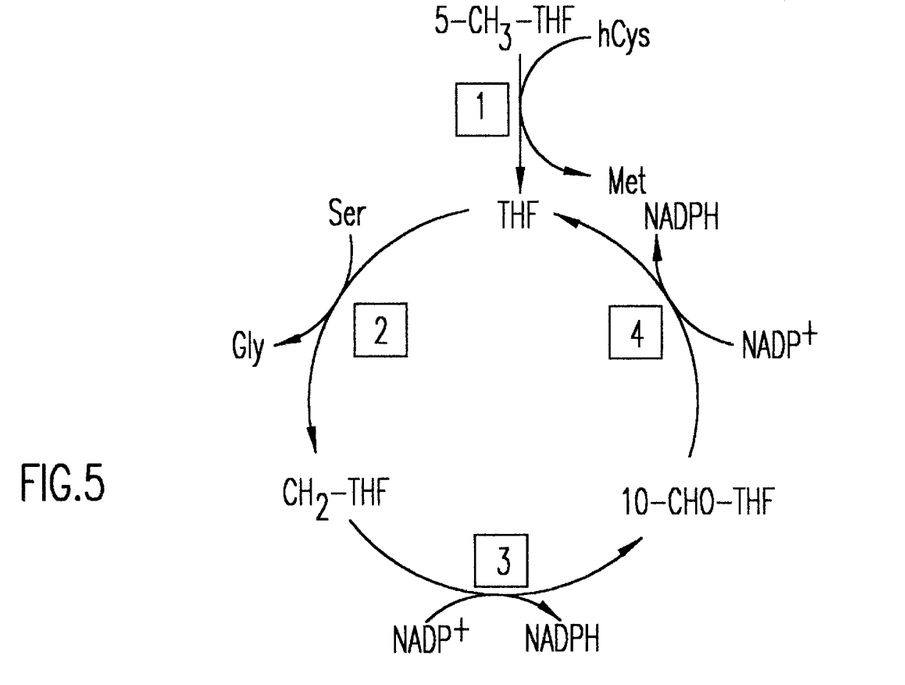
FIG. 5. Reactions for determining hCys as NADPH at 340 nm (Method 2). [1], methionine synthase; [2], SHMT; [3], methylene tetrahydrofolate dehydrogenase; [4], formyl tetrahydrofolate dehydrogenase.

We have previously analyzed folates by utilizing a series of enzymes that cycle tetrahydrofolate during the conversion of serine to glycine (18). The cycling reactions are depicted in FIG. 5 as reactions 2, 3, and 4, and are catalyzed by the enzymes SHMT, methylene tetrahydrofolate dehydrogenase and formyl tetrahydrofolate dehydrogenase, respectively. During each catalytic cycle of FIG. 5, two NADP$^+$ molecules are converted to NADPH for each THF that enters the cycle. THF enters the cycle via Reaction 1, which is catalyzed by methionine synthase. This is the same reaction outlined previously (equation 1) for Method 1. When limiting amounts of enzymes are used, the cycle operates about 50 times per minute. Thus, the molar amount of THF which enters the cycle is amplified 100-fold into NADPH for each minute of incubation (2 NADPH are generated 50 times each minute per molecule of THF).

In a preferred embodiment, Method 2 can be practiced as follows: First, if the biological sample of interest is tissue, it is extracted with dilute acetic acid, which destroys all of the endogenous folates, and then the extract is neutralized. This step requires two minutes. For samples of serum or plasma this extraction step is not required since the levels of hCys greatly exceed the levels of endogenous folates. Dithiothreitol (DTT, 5 mM) is then added to the sample to reduce all disulfide of hCys. A few (typically 10–20) μl of the sample is added to a vial containing methionine synthase (about 20 μg) and 5-CH$_3$-THF (about 10 nmoles) and incubated for 5 min. at 30° C. During this "preincubation", the hCys and 5-CH$_3$-H$_4$THF are converted to methionine and THF. (This is the same first enzymatic reaction as described in Method 1). The remainder of the assay components (SHMT, 200 μg; methylene tetrahydrofolate dehydrogenase, 50 μg; formyl tetrahydrofolate dehydrogenase, 50 μg; and NADP$^+$, ε=6, 240 per M per cm) are then added and the reaction is incubated another 10 minutes. During the 10 minute incubation, the NADP$^+$ is converted to NADPH. At the end of the incubation period, the reaction is stopped (for example, by the addition of a strong buffer which raises the pH to about 10) and the increase in absorbance at 340 nm is determined. NADPH has an absorbance maximum at 340 nm, thus the increase in A$_{340}$ correlates with the amount of NADPH produced during the reaction, and is indicative of the amount of hCys in the original sample. Again, this method requires no separation steps and no derivatization of hCys. The total time required is about 20 minutes or less, and the assay is sensitive in the 2 to 50 pmole range.

Methods 1 and 2 provide distinct advantages over the most commonly used analogous methods for assaying hCys. One distinct advantage is that the final cost will be much less than that of the methods currently used. The final cost of both Method 1 and Method 2 of the present invention will likely be less than 50 cents per assay, a considerable savings. (Compared to the technique that is now most commonly used in research labs, 1000 assays would cost about $500 in lieu of about $7000.) The methods of the present invention are also more sensitive than currently used methods. Method 1 is about 3-orders of magnitude more sensitive than current methods, and Method 2 is about 1 order of magnitude more sensitive. Another important advantage is that the time for analysis will be greatly reduced. The methods of the present invention can measure hCys routinely in about 30 minutes or less. In both methods hCys is converted to methionine to produce THF in a 1:1 molar ratio with the hCys in the sample. The THF is then acted on by enzymatic reagents to produce labeled (or otherwise detectable) substances which correspond directly with the quantity of THF. The level of THF can be determined from the substrates, and this in turn corresponds directly to hCys levels.

Method 2 can be automated more easily than either of the two commonly used methods and would thus be appropriate for volume screening of plasma or serum samples in a clinical laboratory. The entire procedure is done in a single reaction container with no transfers and can thus be readily adapted to run in 96-well ELISA plates with volumes of 200 μl per well. Those of skill in the art will recognize that many such 96-well plate assay systems have already been adapted for automation and that the means for adapting the method of the current invention are readily available.

In a preferred embodiment of the present invention, the second enzymatic reaction of Method 2 is stopped by the addition of a strong buffer which raises the pH to about 10. At this pH, NADPH is stable and at least 2 of the enzymes of the Method 2 are inactive. However, it will be appreciated by those of skill in the art that other means of stopping the reaction may also be appropriate. For example, L-cysteine, which is a powerful inhibitor of SHMT, may be added to the reaction. Any appropriate means of stopping the reactions which provides for the stability of NADPH and which stops the activity of the enzymes may be used in the practice of the invention. Similarly, in a preferred embodiment of the invention, the second enzymatic reaction of Method 1 is stopped by the addition of 10 μl of 10% TCA. However, those skilled in the art will recognize that any appropriate amount of TCA or any other suitable reagent may be used to stop the reaction, so long as it does not interfere with the detection of $^3$H$_2$O.

Method 2 is based on the detection of the product NADPH. In a preferred embodiment of the invention, NADPH is detected directly by spectroscopically analyzing the reaction at 340 nm (extinction coefficient=6240 per mole per cm). However, it will be understood by those of skill in the art that many other means of detecting NADPH are also available and may be used in the practice of this invention. For example, NADPH may be converted to a colored product using nitro blue tetrazolium and phenazine methosulfate. These two reagents give a blue color that is directly proportional to the amount of NADPH and the blue color can then be detected spectrophotometrically or by visual inspection and comparison to a standard color chart. Any appropriate method that results in a detectable form of NADPH that is directly proportional to the amount of NADPH may be used in the practice of the present invention.

Method 1, however, involves using tritiated glycine. Although this could be automated, it is highly unlikely that the use of radioactivity would be acceptable in a clinical lab. Rather, it is envisioned that this method as being used by investigators in research labs, for example those who are measuring hCys levels in cell culture, tissues, the proteins which bind hCys, etc. Most research labs routinely use radioactivity and are appropriately equipped with respect to compliance with safety standards and radioactive waste disposal. For these researchers, automation is not necessarily important but cost and the time required for conducting an assay are of the utmost importance. The exquisite sensitivity of Method 1 (0.1 to 2 pmoles) makes it an ideal system for looking at hCys levels in, for example, cell culture extracts or tissue culture extracts. The methionine synthase can be purified from a recombinant clone of the enzyme. In this clone, production of the enzyme is driven by its natural promoter and thus the amount of methionine synthase that can be produced in a practical manner is limited. For example, in one day from 2 liters of cells, 50 mg of sufficiently pure protein can be obtained, which is enough for about 2000 assays. In a preferred embodiment of the present invention, methionine synthase will be produced from a plasmid in which the cDNA for the enzyme has been cloned with a more powerful promoter. Methods of cloning cDNA into plasmids with powerful promoters are well-known to those of skill in the art and can be readily accomplished. While the source of the methionine synthase used in the experiments reported herein is *Escherichia coli*, it will be readily comprehended by those of skill in the art that methionine synthase from any source (from which suitable quantities of enzyme with appropriate specific activity can be obtained) can be used in the practice of the present invention.

The SHMT used in the experiments reported herein was recombinant *E. coli* SHMT purified according to the method described by diSalvo et al. (19).

Using this method, a person can purify 1.5 grams of SHMT in 2 days from 6 liters of *E. coli* cells to a purity sufficient for these assays. This is enough SHMT to perform 15,000 assays. However, it will be understood by those of skill in the art that SHMT from other sources can also be used in the practice of the present invention. SHMT from any organism that is available in sufficient quantities and purity may be used in the practice of this invention.

The amount of methionine synthase and SHMT used in the preferred embodiments of the present invention are 20 $\mu$g per reaction and 200 $\mu$g per reaction, respectively. However, other concentrations of the enzymes may be used in the practice of this invention. Any appropriate concentration of methionine synthase or SHMT may be used so long as the enzymes are present in excess in the respective reactions.

The enzyme formyl tetrahydrofolate dehydrogenase used in the experiments reported herein was obtained from rabbit liver. The enzyme constitutes 3% of the soluble protein in rabbit liver so this is a preferred source. 90 mg of pure enzyme (enough for about 1800 assays) can be obtained in one day from two rabbit livers so this is an excellent source. However, those of skill in the art will recognize that formyl tetrahydrofolate dehydrogenase from other sources (for example, the cloned enzyme) or from other organisms may also be employed in the practice of this invention.

The enzyme methylene tetrahydrofolate dehydrogenase can be obtained from rabbit liver. In 2 days, 100 mg (or enough for about 2000 assays) can be obtained from 6 rabbit livers. Alternatively, the enzyme can be cloned and this clone can be used as a source of methylene tetrahydrofolate dehydrogenase.

Those of skill in the art will recognize that any appropriate source of sufficiently pure enzyme may be used in the practice of the present invention.

5-methyl-THF is commercially available. Alternatively, 5-methyl-THF can be obtained by the catalytic reduction of folic acid and formaldehyde. Those of skill in the art will recognize that 5-$CH_3$-THF occurs with varying levels of polyglutamylation. It is known that the level of polyglutamylation does not affect the reactions which comprise the methods of the present invention. In a preferred embodiment of the present invention, the level of polyglutamination is from 1 to about 5 because using 5-$CH_3$-THF containing glutamate in excess of about 5 is likely to be prohibitively expensive. However, 5-$CH_3$-THF of any polyglutamination level may be used in the practice of the present invention.

The exact concentration of 5-$CH_3$-THF in a preferred embodiment of the invention is 10 nmoles per reaction. However, those of skill in the art will readily recognize that other concentrations of 5-$CH_3$-THF may be used in the practice of the present invention so long as 5-$CH_3$-THF is in excess.

The tissue which was assayed was rat liver, it will be understood by those of skill in the art that the level of hCys in any biological sample may be assayed by this method. For example, plasma, serum, urine, tissue extracts from any type of tissue, cell culture extracts, protein samples, etc. Biological samples may be pretreated before assay if necessary, for example, tissue samples may be extracted with dilute acid to destroy endogenous folates.

The present invention provides methods for the detection and quantification of hCys in biological samples. One use is to determine whether or not patients in a clinical setting have "elevated" levels of hCys in plasma or serum. The average hCys level for a normal individual is about 7–9 nmol per ml of plasma. If an individual has a level of hCys greater than 15 nmol per ml of plasma, then the person is considered to have elevated hCys. Thus, in the practice of the present invention, a person will be considered to have "elevated" hCys levels if those levels in plasma are greater than about 15 nmol per ml of plasma.

In some biological samples, significant portions of the hCys may be bound by disulfide linkage to circulating proteins (e.g. albumin) and hCys may also be present in the form of other disulfide derivatives (eg. hCys-cysteine conjugates). To obtain an estimate of total hCys it may therefore be desirable to treat the sample with a reducing agent to cleave the disulfide bonds and liberate free hCys. Disulfide are easily and specifically reduced by thiols. In a preferred embodiment of the present invention, disulfide are reduced using DTT. However, it will be understood by those of skill in the art that a wide variety of reducing agents (e.g. dithiothreitol, 2-mercapto-ethanol, cysteine-thioglycolate, thioglycolic acid, glutathione, trialkylphosphines, and the like) are available and may be used in the practice of the present invention.

In chemical analysis in both clinical and research settings, the use of standard curves for calibration purposes is standard practice. Thus, in the practice of the methods of the present invention, samples of known hCys content may be used in the place of clinical or experimental samples to construct a standard curve for the response or signal to be measured. The hCys content of the unknown samples may then be calculated by interpolation from the standard curve.

The methods of the present invention may be carried out in a variety of suitable standard biological buffers which maintain optimal conditions of pH and ionic strength for the reactions of the present invention. For example, 20 mM potassium phosphate, pH 7 to 7.5.

In a preferred embodiment, the incubation temperature for the reactions of methods 1 and 2 is 30° C. The length of enzymatic reaction 1 (the "preincubation") is 10 minutes for Method 1 and 5 minutes for Method 2. The length of enzymatic Reaction 2 for Method 1 is 3 minutes, and the time for the second enzymatic reaction of Method 2 is 10 minutes. However, those of skill in the art will recognize that modifications of the conditions as given in order to optimize such factors as the temperature of incubation and time of incubation may be made. Whatever temperature and times of incubation result in the generation of appropriate amounts of the compounds being detected ($^3H_2O$ in Method 1, NADPH in Method 2) may be used in the practice of this invention.

The assay methods of the present invention may be used for the diagnosis and monitoring of pathological or potentially pathological conditions which are related to or manifested in the hCys content of body fluids or tissues. These include but are not limited to atherosclerosis, blood diseases, vitamin deficiencies, inborn errors of metabolism, and the like. They may also be used for the evaluation of the effects of pharmaceuticals, such as anti-folate drugs. They may also be used in research settings for the investigation of any subject related to hCys, such as one-carbon metabolism, folate metabolism, and the like.

The present invention provides methods of assaying hCys in biological samples. In another aspect of the invention, analytical products are provided which may be in the form of kits. For example, a kit developed from Method 1 of the present invention may include but is not limited to: methionine synthase in a suitable, stable form and quantity; 5-$CH_3$-THF in a suitable, stable form and quantity; SHMT in a suitable, stable form and quantity; [2-$^3H$]glycine; a suitable reducing agent; suitable buffer(s); and hCys samples of known concentration to be used in the generation of a standard curve. A kit developed from Method 2 may include but is not limited to: appropriate quantities and stable forms of the enzymes methionine synthase, SHMT, methylene tetrahydrofolate dehydrogenase and formyl tetrahydrofolate dehydrogenase; 5-$CH_3$-THF in a suitable, stable form and quantity; a suitable reducing agent; suitable buffer(s); $NADP^+$; and hCys samples of known concentration to be used in the generation of a standard curve. The kit components may be packaged separately for mixing by the user, or combined (premixed) in an appropriate manner. The actual container(s) for the kit components may be any which are suitable for carrying out the methods of the present invention. For example, test tubes, multiwell plates, cuvettes, and the like. In addition, the container(s) for containing the reaction components may be multi-chambered or divided in such a manner as to facilitate carrying out the reaction, especially in order to minimize transfers of the solution. For example, the first reaction of Method 1 could be run in an upper chamber of a suitable container, then, after the addition of a Dowex-50 wafer, the entire container could be centrifuged, driving the solvent through the filter and into a detachable lower chamber. The entire lower chamber could then be placed in a counting vial for quantification of radioactivity. The reagents, enzymes and buffers of the present invention may be provided in a manner such that the reactions they catalyze are carried out free in solution. By reagent we mean any non-enzyme component of the method. Alternatively, the reagents and enzymes of the present invention may be provided in a manner such that they are immobilized. For example, they may be attached to an inert support such as polystyrene beads, or to a test strip, or to any inert support that allows the reactions of the methods to be carried out unhindered, and that allows for or facilitates the steps, including the final detection step, for the method. For example, in the practice of Method 2, calorimetric reagents for detecting NADPH could be attached to an inert test strip. Method 2 might then be carried out in environments lacking sophisticated analytical means, such as in developing countries. Using the Method 2 of the present invention, a small sample of blood (such as that obtained from a finger puncture) could be analyzed using a kit containing the assay components of Method 2. The quantity of NADPH produced could be estimated by contacting the final reaction mixture with the test strip which is coated with colorimetric reagents, and matching the amount of color to a standard set or a colored sheet.

The development of detection methods of this type are well known to those of skill in the art. For example, several such test strip methods are available for measuring pH. Also, the enzymes to be utilized in the practice of the present invention may be immobilized to a solid support, such as covalently or noncovalently linked polystyrene beads, and the like.

A useful kit must have a reasonable shelf-life. Thus, the components of the kits of the present must be prepared and packaged in such a way as to insure their stability for a reasonable length of time, typically for several months. All of the enzymes of the present invention are known to be stable for at least 2 years at −20° C. SHMT in 10% sorbitol is stable at 37° C. for up to 500 hours. The enzymes and other components of the present invention may be provided in whatever form or manner insures their stability for the requisite time. For example, stabilizers such as sorbitol, glycerol, dithiothreitol, or ethylenediamine tetraacetate may be added, or the enzymes and components may be stored in sealed vials under nitrogen or argon, or solutions of the components may be made in degassed buffer and filter sterilized into sterile ampules, or the components may be freeze dried. Any condition which results in insuring the stability of the reaction components of the current invention but which does not interfere with the assay of hCys may be used.

In particular, the substrate 5-$CH_3$-THF is known to be labile to oxidation and light. In a preferred embodiment of the invention, 100 mM 2-mercaptoethanol can be used to stabilize this compound for many months at −20° C. However, other stabilizers may also be used, such as the antioxidant ascorbate. Those of skill in the art will recognize that many such antioxidants exist and can be used in the practice of the present invention. Any suitable antioxidant which does not interfere with the reactions of the present invention or the detection of the final product may be used to stabilize 5-$CH_3$-THF.

Method 1 of the present invention is designed to detect the total amount of hCys in a biological sample. To do this, a reducing agent is added to the sample in order to release any bound hCys. However, the method may be adapted to distinguish between bound and free hCys by not adding a reducing agent to a portion of the sample and comparing the results obtained with that portion to that obtained with the reduced portion. Alternatively, a sample may be subfractionated and the amount of hCys (both bound and free) in the various subfractions may be assayed.

Those of skill in the art will recognize that, while the methods of the present invention are directed toward the analysis of hCys in humans, the methods may also be used in the practice of veterinary research and medicine.

The following examples are presented to illustrate various embodiments of the present invention but should not be construed so as to limit the invention in any way.

EXAMPLES

Materials

The enzymes which were used in the examples were obtained as follows:

SHMT was recombinant SHMT, purified as described by diSalvo et al. (19).

The enzymes formyl tetrahydrofolate dehydrogenase and methylene tetrahydrofolate dehydrogenase were obtained from rabbit liver as described by Schirch (20). Methionine synthase was purified as described by Gonzales et al. (21).

Tritiated glycine was obtained from Amersham.

Rabbit serum was obtained from Pel-Freeze Biologicals, Rogers, Ak.

5-$CH_3$-THF was obtained from Sigma. $NADP^+$ was obtained from Sigma. All other reagents were obtained from Sigma.

Determination of % Recovery

A valid assay must provide at least 90% recovery of the substance being assayed. For development of the present invention, % recovery was measured by adding exogenous hCys to the samples, generating a standard curve and determining the Y-intercept of the curve. The Y-intercept gives the amount of added hCys measured by the assay. Dividing this amount by the actual amount added gives the % recovery.

Example 1

Figure 6:
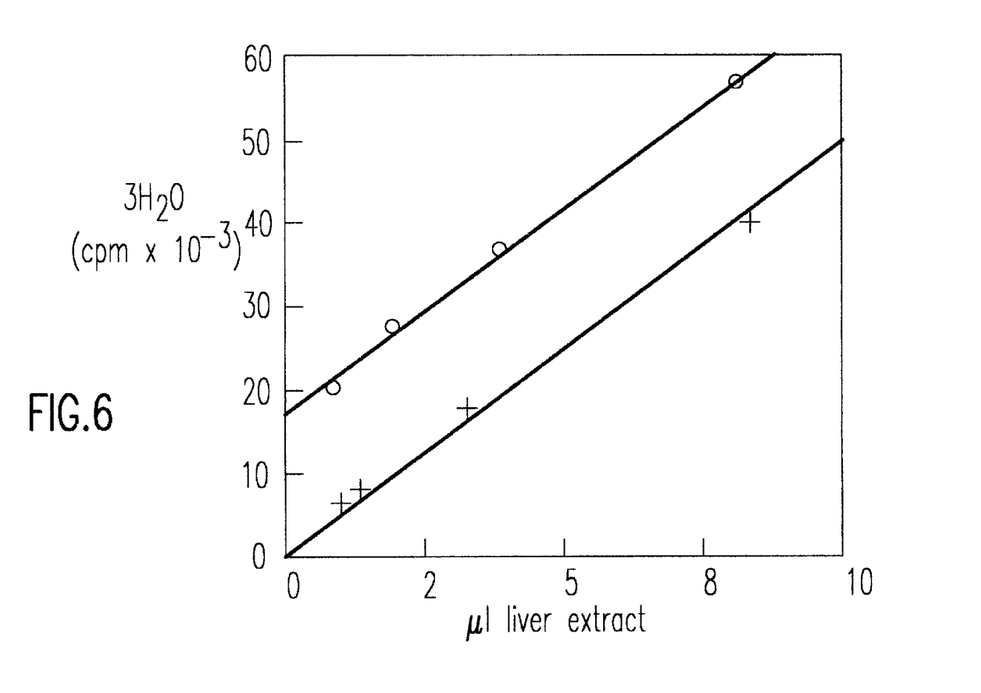
FIG. 6. Rate of solvent exchange of tritium from [2-$^3$H] glycine with increasing amounts of rat liver extract (x). Upper curve (o), same reaction with addition of 0.3 pmol of THF added to liver extract.

Rate of Solvent Exchange of Tritium by SHMT with Increasing amounts of Rat Liver Extract The rate of solvent exchange of tritium by SHMT (enzymatic reaction 2 of Method 1) was determined as a function of the amount of rat liver extract added to the reaction. The results are presented in FIG. 6. As can be seen, the assay is linear with increasing volumes of rat liver extract. The upper curve is the same liver extract that has been spiked with THF (0.3 pmol of THF added to each volume of extract). The y axis intercept is used to calculate the % recovery of the added THF, which in this case is greater that 95%. In this example, assays were performed in triplicate and reported with one standard deviation.

Example 2

Generation of a standard curve for hCys using Method 1

Figure 7:
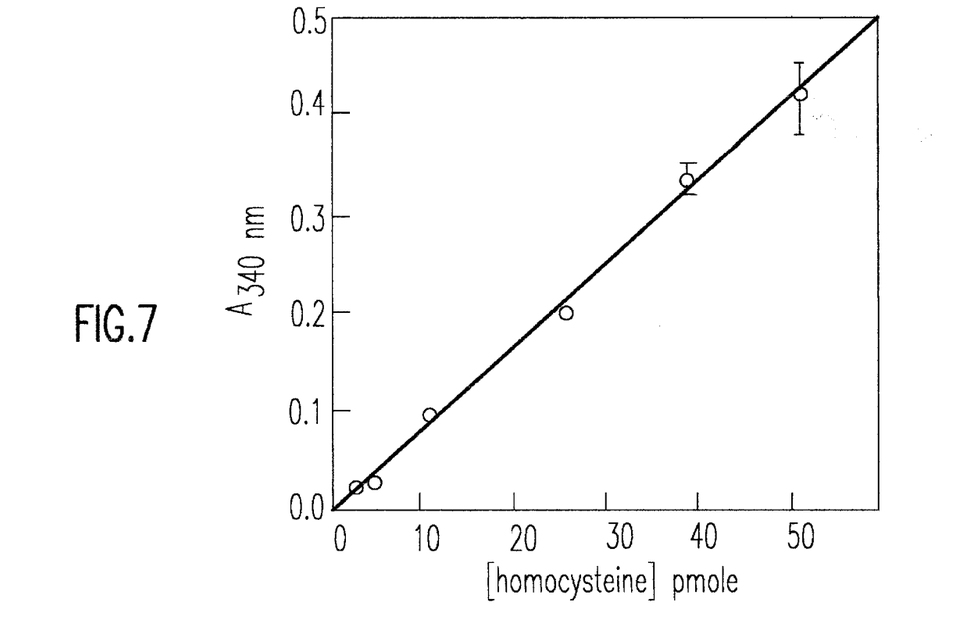
FIG. 7. Standard curve for hCys using the assay procedure of Method 1.

FIG. 7 depicts a standard curve for hCys which was generated by Method 1 as described above. As can be seen, the assay is linear in the 1 to 20 pmole range. The sensitivity for hCys can be increased by 10-fold (i.e. to the 0.1 to 2 pmole range) by using a preparation of [2-H] glycine of higher specific activity. In this example, assays were performed in triplicate and reported with one standard deviation.

Example 3

Generation of a standard curve for hCys using Method 2

Figure 8:
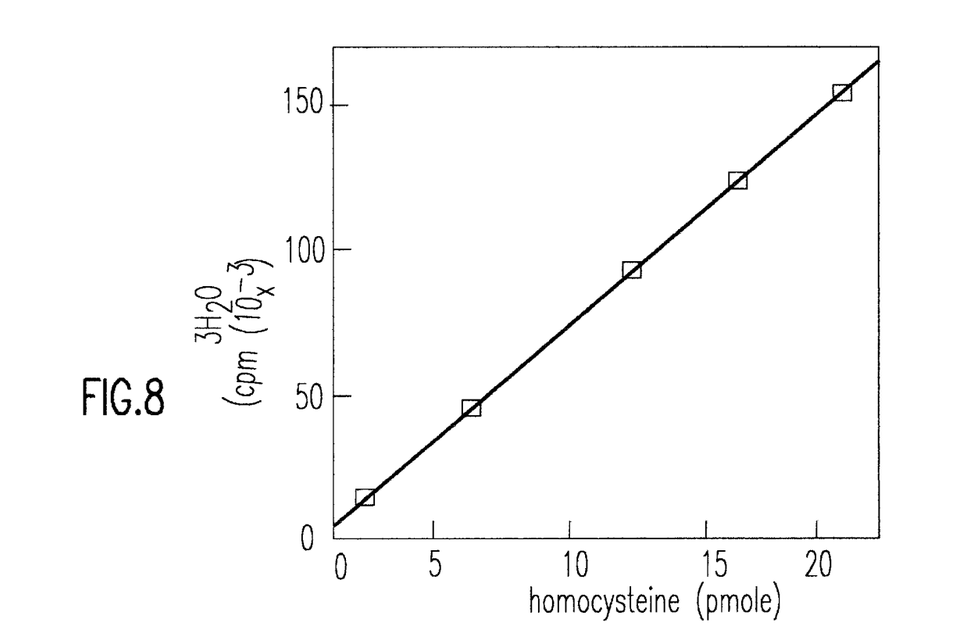
FIG. 8. Standard curve for hCys using the assay procedure of Method 2.

Using Method 2 of the present invention, a standard curve for hCys was generated, and is depicted in FIG. 8. As can be seen, the assay is linear in the 2.0 to 50 pmole range. In this example, assays were performed in triplicate and reported with one standard deviation.

Example 4

Correlation of volume of rabbit serum with hCys level

Figure 9:
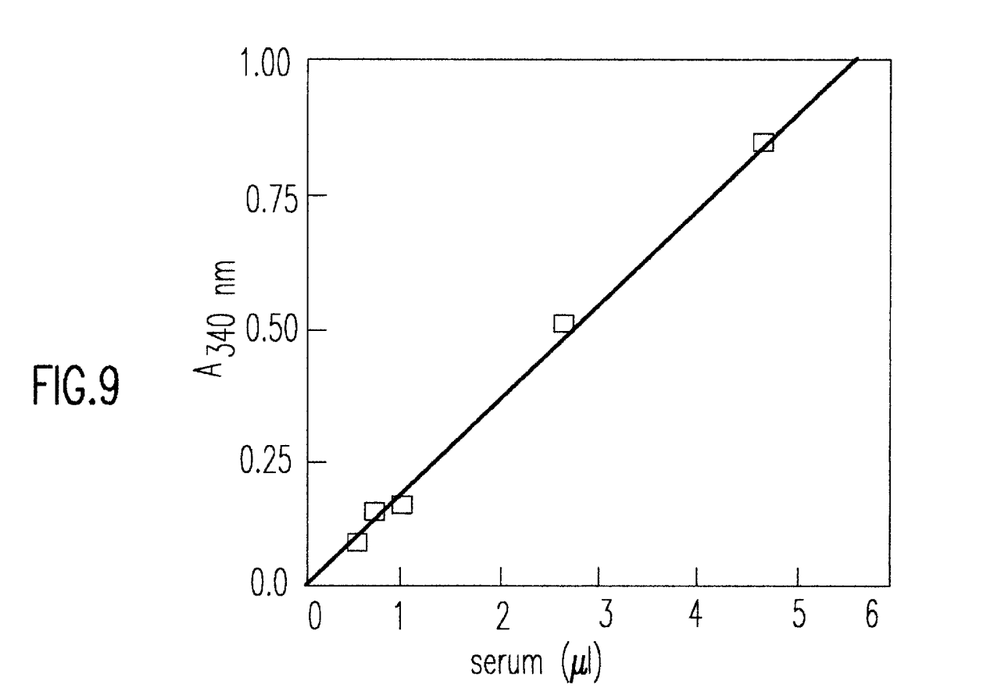
FIG. 9. Correlation of hCys with volume of rabbit serum using the assay procedure of Method 2.

Method 2 of the present invention was used to generate data correlating the volume of rabbit serum in a sample with the amount of hCys detected. The results are given in FIG. 9. As can be seen, the assay is linear in the 2 to 50 picomle range. In this example, assays were performed in triplicate and reported with one standard deviation.

While the invention has been described in terms of its preferred embodiments, those skilled in the art will recognize that the invention can be practiced with modification within the spirit and scope of the appended claims.

REFERENCES

1. Clarke, R., Daly, L., Robinson, K., Naughten, E., Cahalane, S., Fowler, B., and Graham, I. (1991) "Hyperhomocysteinaemia: an independent risk factor for vascular disease" *N.Engl.J.Med.* 324, 1149–1155.
2. Ubbink, J. B. (1994) "Vitamin Nutrition Status and Homocysteine: An Atherogenic Risk Factor" *Nutri. Rev.* 52, 383–387.
3. Green R., and Jacobsen, D. W. (1995) "Clinical Implications of Hyperhomocysteinemia" in Folate Health and Disease, ed. L. B. Bailey, Marcel Dekker, Inc. New York, pp. 75–122.
4. Lucock, M.D., Daskalakis, I., Lumb, C. H., Schorah, C. J., and Levene, M. I. (1998) Impaired regeneration of monoglutamyl tetrahydrofolate leads to cellular folate depletion in mothers affected by a spina bifida pregnancy, *Mol. Gen. Met.* 65, 18–30.
5. Eskes, T. (1998) Open of Closed? A World of Difference: A History of Homocysteine Research, *Nutr. Rev.* 56, 236–244.
6. Jacobsen, D. W. (1998) Acquired hyperhomocysteinemia in heart transplant recipients, *Clin. Chem.* 11, 2238–2239.
7. Hong, S., Yang, D. and Chang, S. Plasma homocysteine, vitamin $B_6$, vitamin $B_{12}$, and folic acid in end-stage renal disease during low-dose supplementation with folic acid, *Am. J Neph.* 18, 367–372.
8. Kuhn, W. et al. (1998) elevated plasma levels of homocysteine in Parkinson's disease, *Euro. Neurol.* 40, 225–227.
9. Jacobs, R., House, J. D., Brosnan, M. E. and Brosnan, J. T. (1998) Effects of streptozotein-induced diabetes and of insulin treatment on homocysteine metabolism in the rat, *Diabetes* 47, 1967–1970.
10. Leeda, M et al. (1998) Effects of folic acid and vitamin $B_6$ supplementation on women with hyperhomocysteinemia and a history of preclampsia or fetal growth restriction, *Am. J Obstet. Gynecol.* 179, 135–139.
11. Austin, et al. (1998) Homocysteine-dependent alterations in mitochondrial gene expression, function and structure: homocysteine and $H_2O_2$ act synergistically to enhance mitochondrial damage, *J. Biol. Chem.* 272, 30808–30817.
12. Karmin, 0. et al. (1998) Homocysteine stimulates the production and secretion of cholesterol in hepatic cells, *Bioch. Bioph. Acta* 1393, 317–324.
13. Geisler, J. et al. (1998) changes in folate status as determined by reduction in total plasma homocysteine levels during Leucovorin modulation of 5-fluorouracil therapy in cancer patients, *Clin. Cancer Res.* 4, 2089–2093.
14. Frantzen, et al. (1998) Enzyme conversion immunoassay for determining total homocysteine in plasma or serum, *Clinical Chemistry,* 44, 311–316.
15. Dias, et al. (1998) Evaluation and intermethod comparison of the Bio-Rad High-Performance Liquid Chromatographic Method for plasma total homocysteine, *Clinical Chemistry*, 44, 2199–2201.
16. Chen, M. S, and Schirch, L. (1973) Serine transhydroxymethylase: studies on the role of tetrahydrofolate, *J Biol. Chem.* 248, 7979–7984.
17. Kim, D. W., Delle Fratte, S., Jeong, S.>and Schirch, V. (1997) The tetrahydrofolate-dependent exchange of glycine protons as a method for determining serine hydroxymethyltransferase and folate levels in cell extracts, *Anal. Biochem.* 253, 201–209.
18. Kruschwitz, H., McDonald, D., Cossins, E. and Schirch, V. (1994) 5-Formyltetrahydro-pteroylpolyglutamates are the major folate derivatives in *Neurospora crassa* conidiospores, *J Biol. Chem.* 269, 28757–28763.
19. diSalvo, M. L., Delle Fratte, S., De Biase, D., Bossa, F., and Schirch, V. (1998) Purification and characterization of recombinant rabbit cytosolic serine hydroxymethyltransferase, *Prot. Express. Purif.* 13, 177–183.
20. Schirch, V. (1997) "Purification of folate-dependent enzymes from rabbit liver", *Methods in Enzymology* vol. 281, 146–161.
21. Gonzalez, J. C., Banerjee, R. V., Huang, S., Sumner, J. S., and Matthews, R. G. (1992) Comparison of cobalamin-independent and cobalamin-dependent methionine synthases from Escherichia coli: two solutions to the same chemical problem, *Biochemistry* 31(26) :6045–56.

We claim:

1. A method for measuring homocysteine in a sample solution, comprising the steps of:
    combining the sample solution with 5-$CH_3$-THF in the presence of methionine synthase;
    forming a THF reaction product from the combined mixture;
    reacting THF with tritiated glycine in the presence of water using serine hydroxymethyltransferase to form tritiated water and non-tritiated glycine; and
    quantifying the amount of tritiated water formed in said reacting step and using the amount of tritiated water formed to identify a level of homocysteine in a sample solution.

2. The method of claim 1 further comprising the step of separating said tritiated water formed in said reacting step from said tritiated glycine.

3. The method of claim 1 further comprising the step of removing endogenous folates from said sample solution prior to said combining step.

4. The method of claim 1 further comprising the step of exposing said sample solution to a reducing agent prior to said combining step.

5. The method of claim 1 wherein said methionine synthase in said combining step and wherein 5-$CH_3$-THF are both present in molar excess quantities.

6. The method of claim 2 wherein said step of separating includes the step of binding said glycine to a solid support.

7. The method of claim 1 further comprising the step of stopping the reaction in said reacting step.

8. The method of claim 1 wherein said combining, forming and reacting steps are performed simultaneously.

9. The method of claim 1 wherein said reacting step is performed after said combining step.

10. A method for measuring homocysteine in a sample solution, comprising the steps of:
    combining the sample solution with 5-$CH_3$-THF in the presence of methionine synthase;
    forming a THF reaction product from the combined mixture;
    reacting THF with serine and $NADP^+$ in the presence of serine hydroxymethyltransferase, methylene tetrahydrofolate dehydrogenase and formyl tetrahydrofolate dehydrogenase; and
    measuring NADPH produced in said reacting step using the amount of NADPH formed to identify a level of homocysteine in a sample solution.

11. The method of claim 10 further comprising the step of stopping the reaction prior to said measuring step.

12. The method of claim 10 further comprising the step of removing endogenous folates from said sample solution prior to said combining step.

13. The method of claim 10 further comprising the step of exposing said sample solution to a reducing agent prior to said combining step.

14. A kit for measuring homocysteine in sample solutions, comprising:
    a reaction vessel;
    quantities of 5-$CH_3$-THF, methionine synthase, serine, $NADP^+$, serine hydroxymethyltransferase, methylene tetrahydrofolate dehydrogenase and formyl tetrahydrofolate dehydrogenase.

15. A kit for measuring homocysteine in sample solutions, comprising:
    a reaction vessel;
    quantities of 5-$CH_3$-THF, methionine synthase, serine hydroxymethyltransferase, and tritiated glycine.

16. A method of detecting hCys in a sample, comprising the steps of:
    enzymatically converting all hCys in a sample to methionine and producing a THF byproduct wherein the amount of THF produced during the enzymatic conversion corresponds directly with the quantity of hCys in said sample; and
    determining an amount of said THF byproduct from said enzymatically converting step, and using said amount to identify a level of hCys in said sample.

17. The method of claim 16 wherein said determining step utilizes at least one enzymatic reaction.

* * * * *